United States Patent [19]

Moore et al.

[11] 4,086,255

[45] Apr. 25, 1978

[54] PERFLUOROALKYLSULFONAMIDOARYL COMPOUNDS

[75] Inventors: George G. I. Moore, Birchwood; Joseph Kenneth Harrington, Edina, both of Minn.

[73] Assignee: Minnesota Mining and Manufacturing Company, St. Paul, Minn.

[21] Appl. No.: 757,883

[22] Filed: Jan. 10, 1977

Related U.S. Application Data

[60] Division of Ser. No. 460,883, Apr. 15, 1974, Pat. No. 4,005,141, which is a continuation-in-part of Ser. No. 268,661, Jul. 3, 1972, abandoned, which is a continuation-in-part of Ser. No. 118,476, Feb. 24, 1971, abandoned, which is a continuation-in-part of Ser. No. 28,148, Apr. 13, 1970, abandoned.

[51] Int. Cl.$^2$ ............................................ C07C 143/75

[52] U.S. Cl. .................... 260/397.6; 260/397.7 DS; 260/465 D; 260/397.7 R; 260/465 E; 260/556 F; 560/12; 560/13

[58] Field of Search ............ 260/397.6, 397.7, 465 D, 260/465 E, 471 C, 556 F

[56] References Cited

U.S. PATENT DOCUMENTS

| | | | |
|---|---|---|---|
| 3,840,527 | 10/1974 | Moore et al. | 260/240 CA |
| 3,906,024 | 9/1975 | Moore et al. | 260/465 E |
| 3,981,914 | 9/1976 | Mutsch et al. | 260/556 F |
| 4,005,141 | 1/1977 | Moore et al. | 260/556 F |

*Primary Examiner*—Cecilia M. S. Jaisle
*Attorney, Agent, or Firm*—Cruzan Alexander; Donald Sell; Donald C. Gipple

[57] ABSTRACT

Phenyl-substituted perfluoroalkanesulfonanilides in which the phenyl rings are linked by sulfur, sulfinyl or sulfonyl and salts thereof in which the rings and the perfluoroalkylsulfonamido nitrogen are optionally substituted. The compounds are active herbicides and some are anti-inflammatory agents and analgesic agents.

16 Claims, No Drawings

PERFLUOROALKYLSULFONAMIDOARYL COMPOUNDS

This is a division of Ser. No. 460,883, filed Apr. 15, 1974, now U.S. Pat. No. 4,005,141, which is a continuation-in-part of copending application Ser. No. 268,661 filed July 3, 1972, itself a continuation-in-part of application Ser. No. 118,476 filed Feb. 24, 1971, which was a continuation-in-part of application Ser. No. 28,148 filed Apr. 13, 1970, applications Ser. No. 268,661, Ser. No. 118,476 and Ser. No. 28,148 being now abandoned.

This invention relates to phenyl-substituted perfluoroalkanesulfonanilides in which the phenyl rings are linked by sulfur, sulfinyl, or sulfonyl and salts thereof in which the rings and the perfluoroalkylsulfonamido nitrogen are optionally substituted. The compounds are active herbicides and some are anti-inflammatory agents and analgesic agents. Methods for the preparation and use of the compounds are also included.

Haloalkylsulfonamido-diphenylthioethers, diphenylsulfoxides and diphenylsulfones have been alluded to heretofore. Thus, see British Pat. Nos. 738,758, 854,956 and 856,452 and French Pat. No. 1,188,591. However, perfluoroalkylsulfonamido compounds of the type covered by the present invention are in no way suggested (only chloroalkylsulfonamido compounds being mentioned) nor is herbicidal activity anywhere mentioned.

It is therefore an object of the present invention to provide compounds which are highly effective herbicidal agents.

It is another object of the invention to provide compounds which modify the growth of plants, i.e. which prevent, alter, destroy or otherwise affect the growth of plants.

It is another object of the invention to provide compounds which are anti-inflammatory agents.

It is another object of the invention to provide compounds which act as polymer curing agents.

It is a further object of the invention to provide a method for controlling unwanted plants.

It is a further object of the invention to provide a method for controlling inflammation in mammalian tissue.

It is still another object of the invention to provide herbicidal compositions containing one or more perfluoroalkylsulfonamidoaryl compounds as active ingredients therein.

It is still another object of the invention to provide anti-inflammatory compositions containing one or more perfluoroalkylsulfonamidoaryl compounds as active ingredients therein.

Still other objects will be made apparent by the following specification.

DETAILED DESCRIPTION OF THE INVENTION

According to the present invention, there is provided a class of compounds of the formula

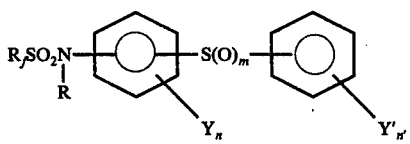

I wherein $R_f$ is a lower perfluoroalkyl radical having one or two carbon atoms, R is hydrogen, cyano, alkyl, alkylsulfonyl, a horticulturally acceptable cation or

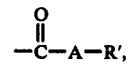

where R' is alkyl and A is oxygen or a carbon-carbon bond, m is 0–2 (zero, one or two), Y is halogen, alkyl, alkoxy, cyano, nitro, amino, alkanamido, hydroxy, dialkylamino, alkoxycarbamoyl, alkylthio, alkylsulfonyl, alkanoyl, dialkylsulfamoyl or alkylsulfinyl, Y' is fluorine, alkyl, alkoxy, cyano, nitro, amino, alkanamido, hydroxy, dialkylamino, alkoxycarbamoyl, alkylthio, alkylsulfonyl, alkanoyl, dialkylsulfamoyl or alkylsulfinyl and n and n' are independently 0–2 (zero, one or two), provided that the individual aliphatic groups appearing in the R, R', Y and Y' moieties contain from one to four carbon atoms each. By alkanamido herein is meant the group alkyl

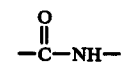

and by alkoxycarbamoyl is meant alkyl

The compounds of Formula I in which R is a cation can also be referred to as salts of the corresponding acid form compounds (i.e. in which R is hydrogen). When n is zero, the phenyl ring bonded to the perfluoroalkylsulfonamido group is unsubstituted except for that group and the group connected thereto through $S(O)_m$. Similarly, when n' is zero (i.e. Y' is H), that phenyl ring is unsubstituted except for the group shown in the formula and attached thereto through $S(O)_m$.

Compounds of the invention wherein $R_f$ is trifluoromethyl are most readily accessible synthetically, and generally most active herbicidally, and are presently preferred.

Preferred subclasses of substituents are those wherein Y is halogen, alkyl, alkoxy, cyano, nitro, amino, alkanamido, hydroxy and alkylsulfonyl and Y' is fluorine, alkyl, alkoxy, nitro, amino, alkanamido and hydroxy.

Compounds of the invention wherein R is hydrogen or a cation are presently preferred. Preferably, also, the individual aliphatic groups in $R_f$, R, R', Y and Y' contain one or two carbon atoms. Presently it is preferred that Y is halogen or alkyl of one to four carbon atoms and Y' is fluorine or alkyl of one to four carbon atoms.

A presently preferred subclass of compounds of the invention includes those compounds in which $R_f$ is trifluoromethyl, R is hydrogen, a cation or

Y is halogen or alkyl of one or two carbon atoms in the 2 position with respect to the trifluoromethylsulfonamido group, the group

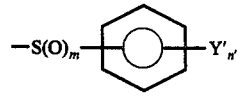

is oriented meta or para to the trifluoromethylsulfonamido group, $n$ and $m$ are zero, one or two, $n'$ is zero or one, and $Y'$ is fluorine, (preferably para) when $n'$ is one. These compounds are preferred as a class because they generally demonstrate good herbicidal activity versus nutsedge (Cyperus spp.) in greenhouse studies, and also show crop selectivity. It should be noted that many other compounds of the invention show these desirable properties, but are not included in the subclass defined above.

The compounds of the invention are acidic when R is hydrogen. Consequently, they form salts, i.e. compounds of formula I wherein R is a pharmaceutically or agriculturally acceptable cation. These are generally metal, ammonium and organic amine salts and can be prepared by treating the acid form (compounds of Formula I in which R is hydrogen) with a stoichiometrically equivalent amount of an appropriate base under mild conditions. Among the metal salts of the invention are alkali metal (e.g. lithium, sodium and potassium), alkaline earth metal (e.g. barium, calcium and magnesium) and heavy metal (e.g. zinc and iron) salts as well as other metal salts such as aluminum. Appropriate bases for use in preparing the metal salts include metal oxides, hydroxides, carbonates, bicarbonates and alkoxides. Some salts are also prepared by cation exchange reactions (by reacting a salt of the invention with an organic or inorganic salt in a cation exchange reaction). The organic amine salts include the salts of aliphatic (e.g. alkyl), aromatic and heterocyclic amines, as well as those having a mixture of these types of structures. The amines useful in preparing the salts of the invention can be primary, secondary or tertiary and preferably contain not more than 20 carbon atoms. Such amines include, for example, morpholine, methyl cyclohexylamine, glucosamine, amines derived from fatty acids, etc. The amine and ammonium salts can be prepared by reacting the acid form with the appropriate organic base or ammonium hydroxide. The pharmaceutically acceptable salts are generally the alkali metal, alkaline earth, ammonium and amine salts. Any of the salts of the types set out above are agriculturally acceptable, the one chosen depending upon the particular use and upon the economics of the situation.

The salts of the invention are frequently formed by reacting the precursors in aqueous solution. This solution can be evaporated to obtain the salt of the compound, usually as a dry powder. In some cases, it may be more convenient to use a non-aqueous solvent such as alcohols, acetone, etc. The resulting solution is then treated to remove the solvent, for example, by evaporation under reduced pressure. Since many of the salts are water soluble, they are often used in the form of aqueous solutions. Also, they can be used in making pharmaceutical preparations in the form of capsules for oral administration.

The compounds of this invention wherein R is hydrogen (the acid form) are prepared by two different methods from precursors (i.e. compounds not falling within the scope of Formula I) and, in addition, certain of the compounds of Formula I are prepared from other compounds of Formula I.

Preparation of the Compounds of Formula I from Precursors

Method A

This is the most general process and can be described as

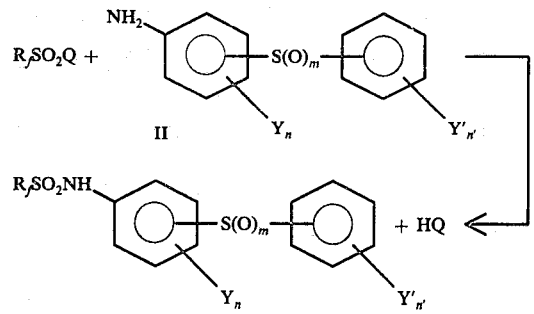

where Q is halogen or the corresponding anhydride residue $OSO_2R_f$, and $R_f$, $Y$, $Y'$, $m$, $n$ and $n'$ are as previously defined. The reaction is usually run in the presence of a suitable acid acceptor, which may be an organic or inorganic base. When Q is halogen it is preferably fluorine or chlorine, and most preferred is fluorine.

A solution of the appropriate primary arylamine of Formula II and at least an equimolar quantity of a suitable acid acceptor (such as dimethylaniline or triethylamine) in an inert organic solvent is prepared. Among the suitable solvents are glyme, benzene, dichloromethane and chloroform. An equimolar quantity of the appropriate perfluoroalkanesulfonic anhydride or halide is added to the solution. The addition is advantageously carried out at $-15°$ to $150°$ C., but this may be raised or lowered if desired. In cases where the amine is of lower reactivity, it is advantageous to allow the reaction mixture to remain at reflux temperature for a few hours following addition.

After completion of the reaction, the product is isolated by conventional methods. For example, the reaction mixture can be extracted with excess aqueous sodium hydroxide. The aqueous extract is then washed with organic solvents and treated with charcoal to remove impurities. Subsequent acidification of the aqueous extract with mineral acid then affords the product as an oil or solid which is distilled, sublimed, chromatographed or recrystallized as required to give pure product. When water-soluble solvents are used, the reaction mixture can be poured directly into aqueous mineral acids. The product is then isolated by conventional extraction techniques and purified as above.

The reaction may also be run in a closed reactor, and when this is done solvent is not usually necessary, and Q is usually fluorine, although an acid acceptor, generally triethylamine, is necessary. The temperatures utilized depend on the reactivity of the reactants, but may be between $0°$ and $200°$ C., and are generally $50°$ to $150°$ C.

Method B

Some of the compounds of the invention can also be prepared by the nucleophilic displacement reaction of a metal salt of an aromatic compound with a halogen derivative or diazonium salt as follows:

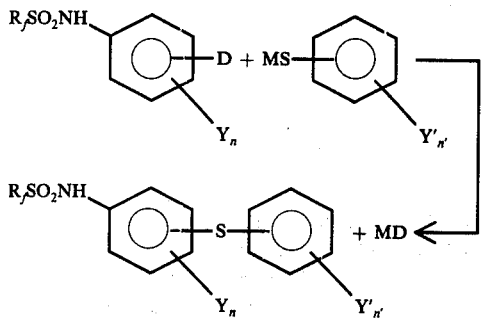

wherein D is halogen (chlorine, bromine or iodine) or a diazonium group (e.g. $-N\equiv N^{\oplus} \, Cl^{\ominus}$), M is an alkali metal, provided that when D is halogen, M can also be copper. The following two specific methods are included within B.

Method B 1.

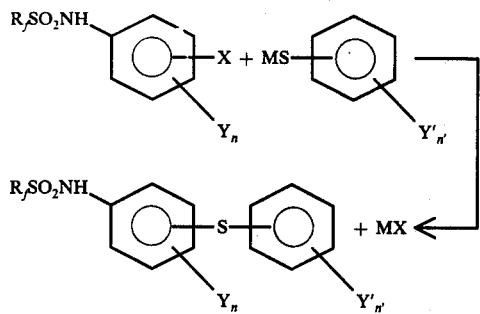

where Y, Y', $n$, $n'$, M and $R_f$ are as previously defined and X is halogen (chlorine, bromine or iodine). Solvents used in the reaction are pyridine-quinoline mixtures or dimethylformamide. Temperatures of 125° to 200° C. are generally necessary to obtain reaction. The reaction is generally run in the presence of a base, which serves as an acid acceptor. Suitable bases may be organic, for example pyridine, or inorganic, for example sodium bicarbonate. The reaction time is usually 6 hours to 3 days, and extended reaction periods are frequently necessary to obtain appreciable reaction.

M must be copper unless Y is an electron-withdrawing group, then M may be an alkali metal. When M is copper the solvent is preferably pyridine-quinoline. When M is an alkali metal, dimethylformamide is a suitable solvent.

The thiophenols and their salts used in the above procedures are known in the chemical literature. The substituted perfluoroalkanesulfonanilide derivatives are known in the chemical literature and are described in South African patent 68/4125, or can be prepared by the methods described in said patent from known starting materials.

Method B-2.

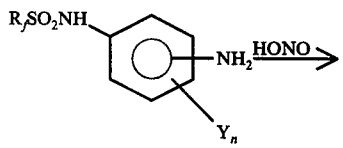

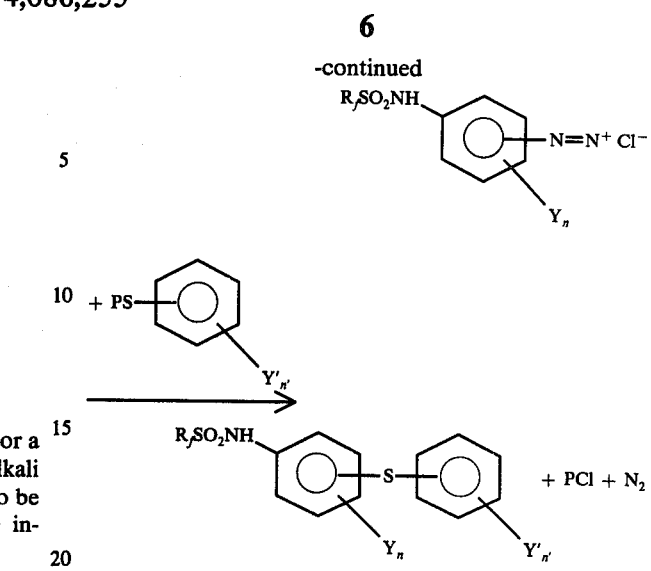

where $R_f$, Y, Y', $n$, and $n'$ are as defined above and P is an alkali metal. This reaction is carried out by adding the cold diazonium salt solution to the refluxing aqueous solution of the alkali metal thiophenoxide salt.

Preparation of Compounds of Formula I From Other Compounds of Formula I

Method C

This method is used to prepare diarylsulfoxides and diarylsulfones by oxidation of the diarylthioethers as follows:

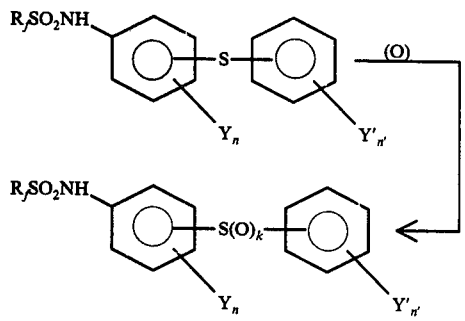

where $R_f$, Y, Y', $n$ and $n'$ are as previously defined and $k$ is one or two. Suitable oxidizing agents are well known to the art, for example hydrogen peroxide, peracids such as peracetic and perbenzoic acid, sodium metaperiodate and the like.

Method D

This method includes the various ways in which Y and Y' are changed in the compounds of Formula I. For example, compounds wherein Y or Y' is amino are prepared by reduction of nitro compounds. Compounds wherein Y or Y' is alkanamido are prepared by acylation of amino compounds. Compounds of Formula I wherein R is hydrogen can be nitrated or halogenated on the phenyl rings. When Y or Y' is alkylthio it is readily oxidized to alkylsulfinyl or alkylsulfonyl. Compounds wherein Y or Y' is hydroxy and R is hydrogen are preferably prepared by simple hydrogen iodide cleavage of the corresponding compound wherein Y or Y' is alkoxy. When Y or Y' is amino, it can be converted to dialkylamino by known methods.

Method E

This method includes the various ways in which R is changed in compounds of Formula I. The preparation of the salts (wherein R is a cation) from compounds in the acid form has already been discussed. To prepare the compounds of the invention wherein R is lower alkyl, compounds of Formula I wherein R is a metal ion, for example sodium or potassium, are reacted with a stoichiometric amount of an alkyl bromide or iodide or a dialkyl sulfate in a nonreactive solvent such as acetone.

Compounds of the invention wherein R is cyano are prepared by reacting the corresponding compounds of the invention wherein R is a cation such as sodium or potassium with cyanogen chloride or bromide in a nonreactive solvent.

Compounds of the invention wherein R is alkylsulfonyl are prepared by reacting the corresponding compounds of the invention wherein R is a cation such as sodium or potassium with an alkylsulfonyl halide (e.g. an alkylsulfonyl chloride).

Compounds of the invention wherein R is a

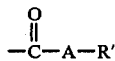

radical are prepared by reacting the corresponding compounds wherein R is a cation with an acylating agent of the formula

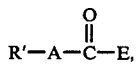 III wherein A and R' are as defined hereinabove and E is halogen, preferably fluorine, chlorine or bromine, or the residue of an anhydride, i.e. an acyloxy group.

Precursors

Suitable perfluoroalkanesulfonyl anhydrides and halides (for example chlorides and fluorides) for use in preparing compounds of Formula I are known to the art. The primary arylamines of Formula II are also either known to the art, or may be made by methods well known to the art, generally by the reduction of the corresponding nitro compounds. Conventional reduction techniques, both chemical and catalytic, well known to the art are used, such as iron in acetic acid, sodium sulfide and, most commonly Raney nickel and hydrogen gas. The nitro compound precursors of the compounds of Formula II are also known to the art, or may be prepared by well known methods, as described [Methods (1) – (5)] and exemplified hereinafter.

Method (1)

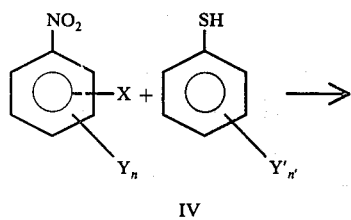

IV

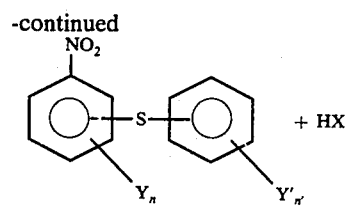

where Y, Y', $n$ and $n'$ are as previously defined, and X is chlorine, bromine or iodine. Although the reaction may be run in the presence of a base which acts as an accelerator and acid acceptor, it is preferably carried out by prereacting the compound of Formula IV with base to form a salt, and salts of inorganic bases are preferred. It is well known that such salts are readily prepared, and they may be prepared in situ, or isolated. Most preferred are salts of alkali metals, such as sodium and potassium, or cuprous salts. When alkali metal salts are used, dimethylformamide and pyridine are preferred solvents.

Cuprous salts are particularly useful for the preparation of 3-phenylthionitrobenzene derivatives, and in this case X is generally not chlorine. When cuprous salts are used, a preferred solvent mixture is quinoline and pyridine.

Method (2)

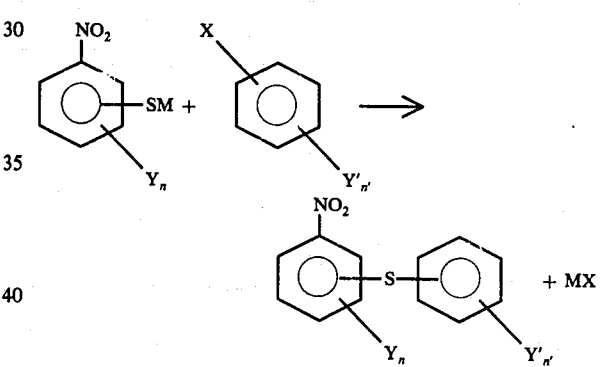

where Y, Y', X, M, $n$ and $n'$ are as previously defined, provided that M is preferably copper in the cuprous form. When Y' is an electron-withdrawing group M may be an alkali metal, but in all cases it is preferred that M is copper and X is bromine or iodine. A cuprous catalyst can also be used.

Method (3)

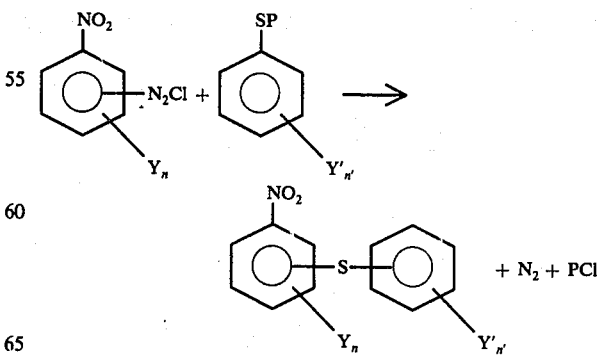

where Y, Y', P, $n$ and $n'$ are as previously defined.

Method (4)

The compounds of Formula II wherein m is one or two can be prepared by the oxidation of the nitro compounds which are precursors of compounds of Formula II wherein m is zero. This oxidation is done using conventional agents such as hydrogen peroxide, sodium metaperiodate and the like.

Method (5)

The nitro compounds which are precursors of compounds of Formula II wherein m is two can be prepared by the Friedel-Crafts reaction as follows:

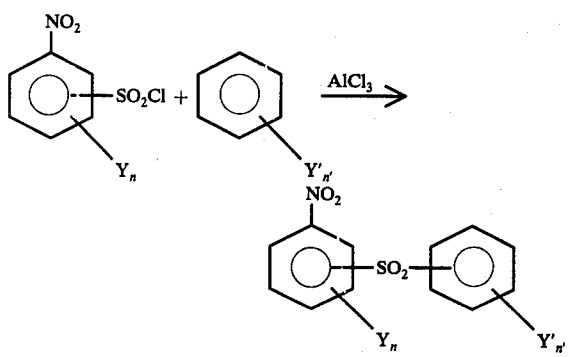

The starting materials necessary for use in Methods (1), (2), (3), (4) and (5) are known to the art and are in the general chemical literature.

A wide variety of acylating agents of Formula III can be used in preparing the compounds of the invention, including acyl halides or anhydrides, haloformates and the like. These compounds are either available directly, or in the case of certain chloroformates are easily prepared from phosgene and the appropriate alcohol.

As noted previously, the compounds of the invention are active herbicides and some are also anti-inflammatory agents. In addition, some have been found to possess anti-microbial activity.

Some compounds of the invention are acidic and are also useful as catalysts or initiators for certain polymerizations, the compounds wherein R is H being particularly useful in this regard. When so used, the compounds are mixed with monomer or prepolymer. Suitable monomers include epoxide and vinyl ether monomers. The rate of reaction and the degree of polymerization varies depending upon the temperature at which the polymerization is carried out and the reactivity of the monomer, and heating of the polymerization reaction is generally utilized to obtain a faster polymerization rate.

The herbicidal activity of representative compounds of Formula I has been determined using screening tests against greenhouse plantings. Both pre- and post-emergence activity are determined in a direct screen against selected weed species. The following weeds are examples of weeds which are used for these tests.

Grasses:
  Giant foxtail (*Setaria faberii*)
  Barnyard grass (*Echinochloa crusgalli*)
  Crabgrass (*Digitaria ischaemum*)
  Quackgrass (*Agropyron repens*)
Broadleaves:
  Pigweed (*Amaranthus retroflexus*)
  Purslane (*Portulaca oleracea*)
  Wild Mustard (*Brassica kaber*)
  Wild Morning glory (*Convolvulus arvensis*)

The test chemicals are dissolved in a small amount of acetone or other suitable solvent and then diluted with water to give a concentration of 2000 ppm. From this concentration aliquots are diluted to give a final concentration of 500 ppm. Eighty ml. of this solution are added to a 6-inch pot containing the weed seeds to give a concentration equivalent to 20 lb./acre. Use of 20 ml. of said solution gives a concentration equal to 5 lb./acre. All subsequent waterings are made from the bottom. Two pots are used per treatment. Data are taken two to three weeks after treatment and recorded as percent pre-emergence kill for each species compared to the untreated controls.

To assess post-emergence activity, the same weed mixtures are allowed to grow from two to three weeks until the grasses are approximately 1 to 3 inches and the broadleaves 1½ inches tall. They are sprayed for approximately 10 seconds or until good wetting of the leaf surfaces occurs with a 2000 ppm solution as described above.

Data are taken two to three weeks after treatment and recorded as percent kill for each species compared to the untreated controls.

The compounds of this invention are broadly active as herbicides. The mechanism(s) by which this herbicidal activity is effected is not presently known. However, many of the compounds of this invention also show various types of plant growth modifying activity. Plant growth modification as defined herein consists of all deviations from natural development, for example defoliation, stimulation, stunting, retardation, desiccation, tillering, dwarfing, regulation and the like. This plant growth modifying activity is generally observed as the compounds of the invention begin to interfere with certain processes within the plant. If these processes are essential, the plant will die if treated with a sufficient dose of the compound. However, the type of growth modifying activity observed varies among types of plants. It has been found that with certain compounds of the invention, herbicidal activity can be separated from certain desirable growth modifying activities by controlling the rate of application. Of particular interest is the ability of some compounds of the invention to give tobacco sucker control. This phenomenon is known to the art to be desirable and useful, since the control of tobacco suckers increases the useful yield of the tobacco plant. This desirable and useful activity is present in a particularly high degree in 2-methyl-4-phenylthiotrifluoromethanesulfonanilide and 2-nitro-4-phenylthiotrifluoromethanesulfonanilide.

As previously noted, some of the compounds of the invention have been found to be particularly effective in controlling nutsedge (for example *Cyperus esculentus* and *Cyperus rotundus*) species. Nutsedge is considered one of the major weed pests of the world. This weed is resistant to most herbicides, and has become an increasingly severe problem. It is a particularly severe problem when other weed species are controlled by herbicides and nutsedge becomes the dominant weed. It was unexpected to find outstanding control of nutsedge in the compounds of the invention.

Presently preferred herbicidal compounds of this invention are:
3-(4'-fluorophenylsulfonyl)trifluoromethanesulfonanilide,
3-Phenylsulfinyltrifluoromethanesulfonanilide,
2-Chloro-4-phenylsulfonyltrifluoromethanesulfonanilide, 2-Methyl-5-phenylsulfinyltrifluoromethanesulfonanilide,
4-Methyl-3-phenylsulfinyltrifluoromethanesulfonanildide,
4-(4'-Fluorophenylthio)-2-methyltrifluoromethanesulfonanilide,
4-(4'-Fluorophenylthio)trifluoromethanesulfonanilide,
3-Methyl-4-phenylsulfinyltrifluoromethanesulfonanilide,
2-Phenylthiotrifluoromethanesulfonanilide,
2-Ethyl-4-phenylthiotrifluoromethanesulfonanilide,
3-Phenylthiotrifluoromethanesulfonanildide,
4-(4'-Fluorophenylsulfonyl)-2-methyltrifluoromethanesulfonanilide,
4-Phenylthiotrifluoromethanesulfonanilide,
2,6-Dimethyl-4-phenylthiotrifluoromethanesulfonanilide,
5-Chloro-2-methyl-4-phenylsulfinyltrifluoromethanesulfonanilide,
2-Methyl-4-phenylsulfinyltrifluoromethanesulfonanilide,
2-Ethyl-4-phenylsulfinyltrifluoromethanesulfonanilide,
2,6-Dimethyl-3-phenylsulfonyltrifluoromethanesulfonanilide,
2-Ethyl-6-methyl-4-phenylthiotrifluoromethanesulfonanilide,
2-Methyl-4-phenylthiotrifluoromethanesulfonanilide,
2-Ethyl-6-methyl-4-phenylsulfinyltrifluoromethanesulfonanilide,
2-Methyl-4-phenylsulfonyltrifluoromethanesulfonanilide,
4-Phenylsulfonyl-2-nitrotrifluoromethanesulfonanilide,
4-(2'-Methylphenylsulfinyl)trifluoromethanesulfonanilide,
4-Phenylsulfonyltrifluoromethanesulfonanilide,
2-Ethyl-4-phenylsulfonyltrifluoromethanesulfonanilide,
2-Methyl-3-phenylthiotrifluoromethanesulfonanilide,
2,6-Diethyl-4-phenylsulfonyltrifluoromethanesulfonanilide,
4-Phenylsulfinyltrifluoromethanesulfonanilide,
2,6-Dimethyl-4-phenylsulfinyltrifluoromethanesulfonanilide,
2-Methyl-5-phenylthiotrifluoromethanesulfonanilide,
2-Ethyl-6-methyl-4-phenylsulfonyltrifluoromethanesulfonanilide,
3-Phenylsulfonyltrifluoromethanesulfonanilide,
N-carbethoxy-2-methyl-4-phenylsulfonyltrifluoromethanesulfonanilide,
2,6-Dimethyl-4-phenylsulfonyltrifluoromethanesulfonanilide,
4-Phenylsulfonyltrifluoromethanesulfonanilide, and
N-Carbethoxy-2-methyl-4-phenylthiotrifluoromethanesulfonanilide.

For application to plants, the compounds can be finely divided and suspended in any of the usual aqueous media. In addition, spreading agents, wetting agents, sticking agents or other adjuvants can be added as desired. Dry powders, as such or diluted with inert materials such as diatomaceous earth, can likewise be used as dusts for this purpose. The preparations are coated on the plants or the ground is covered when pre-emergence control is desired. Application is made with the usual sprayers, dust guns and the like. Application rates are at 0.5 to 20 lbs./acre in general, but may be increased or reduced according to individual circumstances of use.

When it is desired to maximize the weed spectrum to be controlled, or to better control a weed not well controlled by specific compounds of the invention, they may be used in combination with other herbicides such as phenoxy herbicides, e.g. 2,4-D; 2,4,5-T, silvex and the like, carbamate herbicides, thiocarbamate and dithiocarbamate herbicides, substituted urea herbicides, e.g. diuron, monuron, and the like, triazine herbicides, e.g. simazine and atrazine, chloroacetamide and chlorinated aliphatic acid herbicides, chlorinated benzoic and phenylacetic acid herbicides such as chloramben and other herbicides such as trifluralin, paraquat, nitralin and the like. Furthermore, herbicidal compositions containing compounds of the invention may contain, in addition, nematicides, fungicides, insecticides, fertilizers, trace metals, soil conditioners, plant growth regulators and the like.

Since certain compounds of the invention are particularly active against nutsedge, it is particularly advantageous to combine them with other known herbicides to broaden the weed spectrum controlled by herbicidal compositions of this invention. Such herbicidal combinations are clearly envisioned in this invention.

The anti-inflammatory activity can be conveniently demonstrated using assays designed to test the ability of these compounds to antagonize the local edema characteristic of the inflammatory response (rat foot edema test) and to inhibit the onset of the erythematous manifestation of inflammation (guinea pig erythema test).

Leading references to the rat foot edema test are:
1. Adamkiewicz, et al, Canad. J. Biochem. Physio. 33:332, 1955;
2. Selye, Brit. Med. J. 2:1129, 1949 and
3. Winter, Proc. Soc. Exper. Biol. Med. 111:554, 1962.

Leading references to the guinea pig erythema test are:
1. Wilhelmi, Schweiz. Wschr. 79:557, 1949 and
2. Winder, et al, arch. Int. Pharmacodyn 116:261, 1958.

Analgesic activity has been observed in standard test methods such as the Randall-Selitto and phenylquinone writhing tests. Anti-inflammatory activity may also be detected by assays known to the art such as the cotton pellet granuloma and adjuvant arthritis tests.

The compounds are preferably administered orally as anti-inflammatory agents but other known methods of administration are contemplated as well, e.g. dermatomucosally (for example dermally, rectally, and the like) and parenterally, for example by subcutaneous injection, intramuscular injection, intravenous injection and the like. Ocular administration is also included. Dosages ordinarily fall within the range of about 1 to 500 mg./kg. of body weight of the mammal to be treated although oral dosages are not usually above 100 mg./kg. and injection dosages are not usually above 50 mg./kg. Suitable forms for oral administration include liquids (such as four percent acacia suspensions), tablets (which may contain anhydrous lactose, microcrystalline cellulose, modified starch, calcium stearate and talc, as well as other conventional compounding agents together with the active anti-inflammatory agent) and capsules. Suitable carriers for topical application include creams, gels, tapes and the like. Liquid formulations, such as solutions or suspensions of the active ingredient in inert carriers, are contemplated for dosage by injection.

The presently preferred compounds of the invention with respect to anti-inflammatory activity include:
4-Nitro-2-phenylthiotrifluoromethanesulfonanilide,
2-Phenylthiotrifluoromethanesulfonanilide,
5-Amino-2-phenylthiotrifluoromethanesulfonanilide,
3-Phenylthiotrifluoromethanesulfonanilide,
and the pharmaceutically acceptable salts of these compounds.

The anti-microbial activity of the compounds is evaluated using a variation of the original agar-plate diffusion method of Vincent and Vincent (e.g. see Vincent, J. G., and Vincent, Helen W., Proc. Soc. Exptl. Biol. Med. 55:162–164, 1944 and Davis, B. D., and Mingioli, E. S., J. Bac. 66:129–136, 1953.

The following examples are given for the purpose of further illustrating the procedures of the present invention, but are not intended, in any way, to be limiting on the scope thereof. Thus, while the great majority of the examples relate to trifluoromethanesulfonanilides, perfluoroethyl groups can be substituted in place thereof. Also, to avoid unduly multiplying the examples which have been selected to illustrate the invention, the examples will relate for the most part to compounds in which R is hydrogen. It is, however, understood that the corresponding compounds in which R is a cation are also easily prepared and are likewise contemplated. Such compounds (in which R is a cation) are also useful as herbicides.

All melting points in the examples are uncorrected. The boiling points and melting points are given in degrees Centigrade and the pressures in millimeters of mercury.

Example 1 relates to the preparation of compounds of Formula I by Method A.

EXAMPLE 1

A mixture of 3-thiophenoxyaniline (20.0 g., 0.099 mole), triethylamine (15.4 ml., 0.11 mole) and chloroform (125 ml.) is treated with trifluoromethanesulfonic anhydride (16.8 ml., 0.10 mole) during a 90 minute period under a nitrogen atmosphere. After stirring ninety minutes, 10 percent hydrochloric acid (150 ml.) is added, the layers are separated, the chloroform fraction is dried and the chloroform is removed in vacuo. The residue is taken up in ten percent sodium hydroxide (150 ml.), the solution is extracted with diethyl ether and the aqueous layer is acidified. An oil forms, and extraction of the aqueous layer with diethyl ether is followed by drying of the ether layer over magnesium sulfate. Fractional distillation yields 3-phenylthiotrifluoromethanesulfonanilide, b.p. 174° C./0.15 mm., m.p. 56.5°–58° C.

| Analysis: | %C | %H |
|---|---|---|
| Calculated for $C_{13}H_{10}F_3NO_2S_2$: | 46.9 | 3.0 |
| Found: | 46.9 | 3.0 |

The following compounds are also prepared using general Method A:
3-(4-methylphenylthio)trifluoromethanesulfonanilide, b.p. 147° C./0.03 mm.
3-(4-methoxyphenylthio)trifluoromethanesulfonanilide, b.p. 197°–201° C./0.22 mm.
3-phenylsulfonyltrifluoromethanesulfonanilide, m.p. 106°–108° C.
2-methyl-5-phenylthiotrifluoromethanesulfonanilide, m.p. 82°–83.5° C.
4-chloro-3-phenylthiotrifluoromethanesulfonanilide, m.p. 82°–85.5° C.
2-methyl-3-phenylthiotrifluoromethanesulfonanilide, m.p. 123.5°–124.5° C.
2-methyl-4-phenylthiotrifluoromethanesulfonanilide, m.p. 100.5°–102° C.
2-methoxy-4-phenylthiotrifluoromethanesulfonanilide, m.p. 75.5°–76.5° C.
2-phenylthiotrifluoromethanesulfonanilide, m.p. 41.5°–44° C.
3-chloro-2-phenylthiotrifluoromethanesulfonanilide, m.p. 63°–63.5° C.
4-chloro-2-phenylthiotrifluoromethanesulfonanilide, m.p. 75°–76.5° C.
5-chloro-2-phenylthiotrifluoromethanesulfonanilide, m.p. 42°–44.5° C.
5-methyl-2-phenylthiotrifluoromethanesulfonanilide, m.p. 54°–55° C.
4-methyl-3-phenylthiotrifluoromethanesulfonanilide, m.p. 59.5°–61.5° C.
3-(2-methoxyphenylthio)trifluoromethanesulfonanilide, b.p. 173°–177° C./0.03 mm.
4-(2-methylphenylthio)trifluoromethanesulfonanilide, m.p. 55°–57° C.
4-(3-methylphenylthio)trifluoromethanesulfonanilide, m.p. 32°–35° C.
4-(4-methylphenylthio)trifluoromethanesulfonanilide, m.p. 72°–74° C.
4-(4-t-butylphenylthio)trifluoromethanesulfonanilide, m.p. 98°–101° C.
4-(3-methoxyphenylthio)trifluoromethanesulfonanilide, m.p. 56°–69° C.
4-(4-methoxyphenylthio)trifluoromethanesulfonanilide, m.p. 79°–84° C.
4-(4-fluorophenylthio)trifluoromethanesulfonanilide, m.p. 72°–74° C.
2-chloro-4-phenylthiotrifluoromethanesulfonanilide, m.p. 97°–101° C.
4-methyl-2-phenylthiotrifluoromethanesulfonanilide, m.p. 47°–50° C.
2-(2-methylphenylthio)trifluoromethanesulfonanilide, m.p. 61°–65° C.
4-(2,4-dimethylphenylthio)-2-methyltrifluoromethanesulfonanilide, m.p. 85°–92° C.
3-methyl-4-phenylthiotrifluoromethanesulfonanilide, m.p. 79°–81° C.
3-chloro-4-phenylthiotrifluoromethanesulfonanilide, m.p. 84°–87° C.
2-methyl-4-(2-methylphenylthio)trifluoromethanesulfonanilide, m.p. 112°–114° C.
2-methyl-4-(4-methylphenylthio)trifluoromethanesulfonanilide, m.p. 105°–107° C.
4-(3-methoxyphenylthio)-2-methyltrifluoromethanesulfonanilide, m.p. 69°–72° C.
4-(4-methoxyphenylthio)-2-methyltrifluoromethanesulfonanilide, m.p. 109°–112° C.
2-methyl-4-(3-methylphenylthio)trifluoromethanesulfonanilide, m.p. 82°–84° C.
3,5-dichloro-4-phenylthiotrifluoromethanesulfonanilide, m.p. 82°–87.5° C.
4-methoxy-2-phenylthiotrifluoromethanesulfonanilide, m.p. 65°–66° C.
4-(4-fluorophenylthio)-2-methyltrifluoromethanesulfonanilide, m.p. 89°–91° C.
2-chloro-5-methyl-4-phenylsulfonyltrifluoromethanesulfonanilide, m.p. 130°–132° C.
5-chloro-2-methyl-4-phenylsulfonyltrifluoromethanesulfonanilide, m.p. 180°–182° C.

3-(2-fluorophenylthio)trifluoromethanesulfonanilide, b.p. 160°-163° C./2.2 mm.

3-(3-fluorophenylthio)trifluoromethanesulfonanilide, b.p. 176°-178° C./1.8 mm.

2,6-dimethyl-3-phenylthiotrifluoromethanesulfonanilide, m.p. 79°-83° C.

4-chloro-3-methyl-2-phenylthiotrifluoromethanesulfonanilide, m.p. 85°-88° C.

2-(3-methylphenylthio)trifluoromethanesulfonanilide, b.p. 120°-122° C./0.04 mm.

Examples 2 and 3 relate respectively to the preparation of compounds of Formula I by Methods B 1. and B 2.

EXAMPLE 2

A slurry of 4-bromotrifluoromethanesulfonanilide (15 g., 0.05 mole), cuprous thiophenolate (10 g., 0.058 mole), sodium bicarbonate (10 g.) and dimethylformamide (100 ml.) is heated at 145° to 150° C. for 2.5 days. The reaction mixture is poured in water (2 liters), the yellow by-product is removed by filtration and the water is acidified to give an oil. This oil is distilled to yield 4-phenylthiotrifluoromethanesulfonanilide, b.p. 159°-163° C./0.5 mm.

| Analysis: | %C | %H | %N |
|---|---|---|---|
| Calculated for $C_{13}H_{10}F_3NO_2S_2$: | 46.8 | 3.0 | 4.2 |
| Found: | 46.3 | 2.9 | 4.3 |

The following compounds are prepared using Method B 1. specifically exemplified in Example 2.

5-chloro-2-methyl-4-phenylthiotrifluoromethanesulfonanilide, m.p. 125°-128° C.

2-fluoro-4-phenylthiotrifluoromethanesulfonanilide, m.p. 74°-78° C.

2,6-dimethyl-4-phenylthiotrifluoromethanesulfonanilide, m.p. 93°-95° C.

2-ethyl-6-methyl-4-phenylthiotrifluoromethanesulfonanilide, m.p. 95°-98° C.

2-isopropyl-4-phenylthiotrifluoromethanesulfonanilide, m.p. 54°-56° C.

5-nitro-2-phenylthiotrifluoromethanesulfonanilide, m.p. 103°-106° C.

5-fluoro-2-methyl-4-phenylthiotrifluoromethanesulfonanilide, m.p. 110°-115° C.

2-chloro-6-methyl-4-phenylthiotrifluoromethanesulfonanilide, m.p. 89°-92° C.

3-chloro-2-methyl-4-phenylthiotrifluoromethanesulfonanilide, m.p. 83.5°-86.5° C.

2,3-dimethyl-4-phenylthiotrifluoromethanesulfonanilide, m.p. 67°-70° C.

2,5-dichloro-4-phenylthiotrifluoromethanesulfonanilide, m.p. 144°-145° C.

2-chloro-3-methyl-4-phenylthiotrifluoromethanesulfonanilide, m.p. 55°-59.5° C.

2-chloro-5-methyl-4-phenylthiotrifluoromethanesulfonanilide, m.p. 121°-123° C.

4-bromo-2-phenylthiotrifluoromethanesulfonanilide, m.p. 90°-93° C. from 4-bromo-2-iodotrifluoromethanesulfonanilide.

4-fluoro-2-phenylthiotrifluoromethanesulfonanilide, m.p. 64°-67° C.

2,3-dichloro-4-phenylthiotrifluoromethanesulfonanilide, b.p. 175°-180° C./2.1 mm.

5-acetamido-2-methyl-4-phenylthiotrifluoromethanesulfonanilide, m.p. 175°-180° C.

4-methylsulfonyl-2-phenylthiotrifluoromethanesulfonanilide, m.p. 140°-142° C.

2,6-diethyl-4-phenylthiotrifluoromethanesulfonanilide, m.p. 92°-95° C.

3-(4-fluorophenylthio)trifluoromethanesulfonanilide, b.p. 157°-162° C./0.03 mm.

3-(3-methylphenylthio)trifluoromethanesulfonanilide, b.p. 156°-160° C./0.05 mm.

3-nitro-4-phenylthiotrifluoromethanesulfonanilide, isolated as the triethylammonium salt, m.p. 110°-112° C.

3-(2-methylphenylthio)trifluoromethanesulfonanilide, b.p. 150°-158° C./0.05 mm.

EXAMPLE 3

A suspension of 2-chloro-5-aminotrifluoromethanesulfonanilide (26 g., 0.085 mole) in water (40 ml.) and concentrated hydrochloric acid (15 ml.) is heated on a steam bath for one hour. More hydrochloric acid (15 ml.) is added and the solution is chilled to 0° to 5° C. sodium nitrite (6 g., 0.085 mole) dissolved in a minimum amount of water is added while maintaining the temperature below 5° C.

A solution of sodium hydroxide (8.6 g.) in water (70 ml.) is heated to 110° C. under a nitrogen atmosphere and thiophenol (18.7 g.) is added. The cold diazonium salt solution is added over one hour, the mixture is stirred an additional thirty minutes, and then made basic with sodium hydroxide solution. This solution is extracted with chloroform, acidified with concentrated hydrochloric acid and then extracted with dichloromethane. The dichloromethane extracts are dried over magnesium sulfate, filtered and the solvent removed in vacuo. The solid 2-chloro-5-phenylthiotrifluoromethanesulfonanilide is recrystallized twice from benzene and dried, m.p. 66°-68° C.

| Analysis: | %C | %H | %N |
|---|---|---|---|
| Calculated for $C_{13}H_9ClF_3NO_2S_2$: | 42.5 | 2.5 | 3.8 |
| Found: | 42.9 | 2.6 | 4.0 |

Examples 4, 5 and 6 relate to the preparation of compounds of Formula I by Method C.

EXAMPLE 4

3-Phenylthiotrifluoromethanesulfonanilide (16.7 g., 0.050 mole) and acetone (25 ml.) cooled to −6° to −2° C. are treated with 30 percent hydrogen peroxide (5.2 ml., 50.8 mmole) in acetone (15 ml.) during ninety minutes. The mixture is stirred until its temperature is about 25° C., and the acetone is removed in vacuo. Benzene is added, then removed in vacuo to azeotrope off any water residue to give an oil. The oil is chromatographed to a florisil column, eluting first with 1:1 benzene:trichloroethylene, then 1:1 benzene:dichloromethane and finally with acetone. The fraction eluting with acetone is dissolved in 10 percent sodium hydroxide solution. This solution is extracted with diethyl ether and the ether extracts are discarded. The solution is then acidified to provide a white gum which is extracted with diethyl ether. The ether layer is dried over magnesium sulfate, the solvent is removed in vacuo and the 3-phenylsulfinyltrifluoromethanesulfonanilide is recrystallized from a trichloroethylene-cyclohexane mixture, then twice from cyclohexane to give a white solid, m.p. 109.5°-111° C.

| Analysis: | %C | %H | %N |
|---|---|---|---|
| Calculated for C$_{13}$H$_{10}$F$_3$NO$_3$S$_2$: | 44.8 | 2.9 | 4.0 |
| Found: | 44.5 | 3.0 | 3.9 |

EXAMPLE 5

2-Methyl-4-phenylthiotrifluoromethanesulfonanilide is dissolved in 50 ml. of acetic acid with heating, then 20 ml. (large excess) of thirty percent hydrogen peroxide is added and heating is continued on a steam bath for three hours. The mixture is poured in 500 ml. of water, extracted with dichloromethane, the organic layers dried over magnesium sulfate then filtered and the filtrate evaporated under vacuum. The residue is recrystallized four times from a benzene-hexane mixture, treating with decolorizing charcoal to give 2-methyl-4-phenylsulfonyltrifluoromethanesulfonanilide, m.p. 138°–139.5° C.

| Analysis: | %C | %H | %N |
|---|---|---|---|
| Calculated for C$_{14}$H$_{12}$F$_3$NO$_4$S$_2$: | 44.3 | 3.2 | 3.7 |
| Found: | 44.8 | 3.3 | 3.6 |

The following compounds are prepared using the general Method C specifically exemplified in Examples 4 and 5.

3-phenylsulfonylperfluoroethanesulfonanilide
2-phenylsulfonyltrifluoromethanesulfonanilide, m.p. 87°–89° C.
Triethylammonium 5-amino-2-phenylsulfonyltrifluoromethanesulfonanilide, m.p. 150°–156° C.
4-phenylsulfonyltrifluoromethanesulfonanilide, m.p. 121°–123° C.
5-nitro-2-phenylsulfonyltrifluoromethanesulfonanilide, m.p. 146.5°–148.5° C.
2-chloro-6-methyl-4-phenylsulfonyltrifluoromethanesulfonanilide, m.p. 140°–146° C.
2,3-dimethyl-4-phenylsulfinyltrifluoromethanesulfonanilide, m.p. 145°–151° C.
2,3-dimethyl-4-phenylsulfonyltrifluoromethanesulfonanilide, m.p. 148°–152° C.
2,5-dichloro-4-phenylsulfonyltrifluoromethanesulfonanilide, m.p. 145°–149° C.
5-fluoro-2-methyl-4-phenylsulfonyltrifluoromethanesulfonanilide, m.p. 181°–185° C.
4-bromo-2-phenylsulfinyltrifluoromethanesulfonanilide, m.p. 181°–185° C.
5-acetamido-2-methyl-4-phenylsulfinyltrifluoromethanesulfonanilide, m.p. 193°–194° C.
4-nitro-2-phenylsulfonyltrifluoromethanesulfonanilide, m.p. 141°–142° C.
2-methyl-5-phenylsulfonyltrifluoromethanesulfonanilide, m.p. 113°–115° C.
4-(4-acetamidophenylsulfonyl)trifluoromethanesulfonanilide, m.p. 233.5°–235° C.
4-(4-acetamidophenylsulfinyl)trifluoromethanesulfonanilide, m.p. 202.5°–204.5° C.
2-methoxy-4-phenylsulfonyltrifluoromethanesulfonanilide, m.p. 117.5°–119° C.
2-methoxy-4-phenylsulfinyltrifluoromethanesulfonanilide, m.p. 124°–126° C.
4-(4-nitrophenylsulfonyl)trifluoromethanesulfonanilide, m.p. 178.5°–180.5° C.
4-(2-methylphenylsulfinyl)trifluoromethanesulfonanilide, m.p. 157°–160° C.
4-(2-methylphenylsulfonyl)trifluoromethanesulfonanilide, m.p. 101°–108° C.
4-(3-methylphenylsulfonyl)trifluoromethanesulfonanilide, m.p. 168°–173° C.
2,6-diethyl-4-phenylsulfonyltrifluoromethanesulfonanilide, m.p. 164°–167° C.
2-ethyl-4-phenylsulfonyltrifluoromethanesulfonanilide, m.p. 131°–134° C.
2-isopropyl-4-phenylsulfonyltrifluoromethanesulfonanilide, m.p. 144.5°–151.5° C.
2-ethyl-6-methyl-4-phenylsulfonyltrifluoromethanesulfonanilide, m.p. 179°–186° C.
2-chloro-5-phenylsulfonyltrifluoromethanesulfonanilide, m.p. 143°–145° C.
2,6-dimethyl-3-phenylsulfonyltrifluoromethanesulfonanilide, m.p. 162°–164° C.
4-methylsulfonyl-2-phenylsulfonyltrifluoromethanesulfonanilide, m.p. 148°–149° C.
3-(2-fluorophenylsulfonyl)trifluoromethanesulfonanilide, m.p. 89°–94° C.
5-acetamido-2-methyl-4-phenylsulfonyltrifluoromethanesulfonanilide, m.p. 169°–173° C.
4-fluoro-2-phenylsulfinyltrifluoromethanesulfonanilide, m.p. 180°–185° C.
4-fluoro-2-phenylsulfonyltrifluoromethanesulfonanilide, m.p. 100°–103° C.
2-fluoro-4-phenylsulfinyltrifluoromethanesulfonanilide, m.p. 131°–134° C.
2-fluoro-4-phenylsulfonyltrifluoromethanesulfonanilide, m.p. 98°–101° C.
5-chloro-2-methyl-4-phenylsulfinyltrifluoromethanesulfonanilide, m.p. 136°–142° C.
2-chloro-5-methyl-4-phenylsulfinyltrifluoromethanesulfonanilide, m.p. 166°–171° C.
4-bromo-2-phenylsulfonyltrifluoromethanesulfonanilide, m.p. 86°–90° C.
4-(4-methylphenylsulfinyl)trifluoromethanesulfonanilide, m.p. 180°–182° C.
4-(4-methylphenylsulfonyl)trifluoromethanesulfonanilide, m.p. 172°–175° C.
4-(4-t-butylphenylsulfonyl)trifluoromethanesulfonanilide, m.p. 219°–223° C.
4-(4-methoxyphenylsulfinyl)trifluoromethanesulfonanilide, m.p. 169°–172° C.
4-(4-methoxyphenylsulfonyl)trifluoromethanesulfonanilide, m.p. 178°–181° C.
4-(2,4-dimethylphenylsulfonyl)-2-methyltrifluoromethanesulfonanilide, m.p. 157°–159° C.
3-methyl-4-phenylsulfinyltrifluoromethanesulfonanilide, m.p. 180°–183° C.
3-methyl-4-phenylsulfonyltrifluoromethanesulfonanilide, m.p. 113°–116° C.
4-(3-methoxyphenylsulfinyl)trifluoromethanesulfonanilide, m.p. 130°–133° C.
3-chloro-4-phenylsulfinyltrifluoromethanesulfonanilide, m.p. 154°–157° C.
3-chloro-4-phenylsulfonyltrifluoromethanesulfonanilide, m.p. 120°–124° C.
2-methyl-4-(2-methylphenylsulfinyl)trifluoromethanesulfonanilide, m.p. 146°–150° C.
2-methyl-4-(2-methylphenylsulfonyl)trifluoromethanesulfonanilide, m.p. 132°–138° C.
2-methyl-4-(3-methylphenylsulfinyl)trifluoromethanesulfonanilide, m.p. 119°–122° C.
2-methyl-4-(3-methylphenylsulfonyl)trifluoromethanesulfonanilide, m.p. 110°–114° C.
2-methyl-4-(4-methylphenylsulfonyl)trifluoromethanesulfonanilide, m.p. 170°–173° C.

3-(2-methylphenylsulfonyl)trifluoromethanesulfonanilide, m.p. 57°–62° C.
3-(4-methylphenylsulfonyl)trifluoromethanesulfonanilide, m.p. 115°–119° C.
2-ethyl-4-phenylthiotrifluoromethanesulfonanilide, m.p. 65°–67° C.
2-nitro-4-phenylsulfonyltrifluoromethanesulfonanilide, m.p. 115.5°–116.5° C.
2,6-dimethyl-4-phenylsulfonyltrifluoromethanesulfonanilide, m.p. 144°–146° C.
4-methyl-3-phenylsulfonyltrifluoromethanesulfonanilide, m.p. 142.5°–145° C.
2-(2-methylphenylsulfonyl)trifluoromethanesulfonanilide, m.p. 91°–94.5° C.
4-methyl-2-phenylsulfonyltrifluoromethanesulfonanilide, m.p. 104°–107° C.
2-(4-methylphenylsulfonyl)trifluoromethanesulfonanilide, m.p. 108°–111° C.
4-(4-fluorophenylsulfonyl)-2-methyltrifluoromethanesulfonanilide, m.p. 128°–133° C.

EXAMPLE 6

To a stirred solution of 4-phenylthiotrifluoromethanesulfonanilide (8.2 g., 0.0246 mole), prepared according to Example 2 and 10 percent sodium hydroxide solution (8.93 ml.) is added sodium metaperiodate (5.27 g., 0.0246 mole). The mixture is stirred for one and one-half hours. Enough 10% sodium hydroxide is added to maintain the solution at a basic pH. The mixture is filtered, and the filtrate is acidified, extracted with chloroform and dried over magnesium sulfate. The solution is filtered and the solvent evaporated in vacuo. The solid 4-phenylsulfinyltrifluoromethanesulfonanilide is recrystallized from isopropyl ether-isopropanol with treatment with decolorizing charcoal to yield an off-white powder, m.p. 164°–166° C.

| Analysis: | %C | %H | %N |
|---|---|---|---|
| Calculated for $C_{13}H_{10}F_3NO_3S_2$: | 44.7 | 2.9 | 4.0 |
| Found: | 45.0 | 3.0 | 4.0 |

The following compounds are prepared using the general Method C specifically exemplified in Examples 4, 5 and 6.
3-(2-methoxyphenylsulfinyl)trifluoromethanesulfonanilide, m.p. 176.5°–178.5° C.
2-phenylsulfinyltrifluoromethanesulfonanilide, m.p. 128°–130° C.
N-methyl-3-phenylsulfinyltrifluoromethanesulfonanilide, m.p. 83°–84.5° C.
2-(3-methylphenylsulfinyl)trifluoromethanesulfonanilide, m.p. 150°–151° C.
2-(2-methylphenylsulfinyl)trifluoromethanesulfonanilide, m.p. 175°–180° C.
3-(3-methoxyphenylsulfinyl)trifluoromethanesulfonanilide, m.p. 79°–88° C.
3-(3,4-dimethylphenylsulfinyl)trifluoromethanesulfonanilide, m.p. 125°–133° C.
2,6-dimethyl-4-phenylsulfinyltrifluoromethanesulfonanilide, m.p. 154°–158° C.
2,6-diethyl-4-phenylsulfinyltrifluoromethanesulfonanilide, m.p. 222°–225° C.
2-ethyl-4-phenylsulfinyltrifluoromethanesulfonanilide, m.p. 153°–156° C.
2-isopropyl-4-phenylsulfinyltrifluoromethanesulfonanilide, m.p. 181°–189° C.
2-ethyl-6-methyl-4-phenylsulfinyltrifluoromethanesulfonanilide, m.p. 171°–176° C.
2-methyl-4-(3-nitrophenylsulfinyl)trifluoromethanesulfonanilide, m.p. 130°–132° C.
4-methylsulfonyl-2-phenylsulfinyltrifluoromethanesulfonanilide, m.p. 140.5°–143.5° C.
4-(4-nitrophenylsulfinyl)trifluoromethanesulfonanilide, m.p. 205.5°–207° C.
4-methyl-3-phenylsulfinyltrifluoromethanesulfonanilide, m.p. 150°–154° C.
2-methyl-4-phenylsulfinyltrifluoromethanesulfonanilide, m.p. 116°–120° C.
4-methyl-2-phenylsulfinyltrifluoromethanesulfonanilide, m.p. 142°–145° C.
2-methyl-5-phenylsulfinyltrifluoromethanesulfonanilide, m.p. 118.5°–122.5° C.
2-(4-methylphenylsulfinyl)trifluoromethanesulfonanilide, m.p. 137°–140° C.

Examples 7–11 relate to the preparation of compounds of Formula I by Method D.

EXAMPLE 7

4-Phenylthiotrifluoromethanesulfonanilide (17.8 g., 0.056 mole) is dissolved in acetic acid (125 ml.), sodium acetate (4.6 g., 0.056 mole) is added then bromine (8.95 g., 0.056 mole) is added over 5 minutes. After stirring one hour the mixture is heated on a steam bath one-half hour, then poured into water (750 ml.). The solid product is recovered by filtration, dissolved in dichloromethane and dried over magnesium sulfate. The solvent is evaporated in vacuo, and the residue dissolved in a benzene-hexane mixture. Triethylamine (excess) is added and the solid product is isolated by filtration, then recrystallized twice from isopropanol, giving triethylammonium 2-bromo-4-phenylthiotrifluoromethanesulfonanilide, m.p. 92°–94° C.

| Analysis: | %C | %H | %N |
|---|---|---|---|
| Calculated for $C_{13}H_9BrF_3NO_2S_2 \cdot C_6H_{15}N$: | 44.4 | 4.7 | 5.45 |
| Found: | 45.1 | 4.9 | 5.5 |

EXAMPLE 8

3-(2-Methoxyphenylthio)trifluoromethanesulfonanilide (16.5 g., 0.045 mole) is placed in glacial acetic acid (65 ml.) and the mixture is heated to reflux temperature (about 130° C.). Excess hydriodic acid (57%, 66 ml.) is added and the mixture is maintained at its reflux temperature for 6 hours, then stirred about 70 hours at room temperature. The mixture is diluted with water, then extracted with dichloromethane. The dichloromethane extracts are combined and dried over magnesium sulfate, then the solvent is removed in vacuo. The solid residue is recrystallized from a mixture of hexane and benzene to give white crystals of 3-(2-hydroxyphenylthio)trifluoromethanesulfonanilide, m.p. 115°–116.5° C.

| Analysis: | %C | %H | %N |
|---|---|---|---|
| Calculated for $C_{13}H_{10}F_3NO_3S_2$: | 44.7 | 2.9 | 4.0 |
| Found: | 44.5 | 2.9 | 4.0 |

The following compound is prepared using the method of Example 8.
4-hydroxy-2-phenylthiotrifluoromethanesulfonanilide, m.p. 93.5°–94.5° C.

EXAMPLE 9

4-(4-Nitrophenylthio)trifluoromethanesulfonanilide (54.0 g., 0.143 mole) in ethanol is reduced over Raney nickel at about 45 psi. After hydrogen uptake is complete the mixture is deactivated with sulfur, filtered, then the filtrate is evaporated in vacuo to a solid which is recrystallized thrice from benzene and decolorizing charcoal to give a tan solid 4-(4-aminophenylthio)trifluoromethanesulfonanilide, m.p. 116.5°–118° C.

| Analysis: | %C | %H | %N |
|---|---|---|---|
| Calculated for $C_{13}H_{11}F_3N_2O_2S_2$: | 44.8 | 3.2 | 8.0 |
| Found: | 45.0 | 3.2 | 8.1 |

The following compounds are prepared using the method of Example 9, or alternatively palladium on charcoal may be used as the reduction catalyst.

3-amino-4-phenylthiotrifluoromethanesulfonanilide, isolated as the triethylammonium salt, m.p. 106°–108.5° C.

4-amino-2-phenylthiotrifluoromethanesulfonanilide, isolated as the triethylammonium salt, m.p. 128°–130° C.

5-amino-2-phenylthiotrifluoromethanesulfonanilide, m.p. 103°–106° C.

EXAMPLE 10

4-(4-Aminophenylthio)trifluoromethanesulfonanilide (43.0 g., 0.123 mole) is dissolved in glacial acetic acid (150 ml.) and treated with acetic anhydride (12.6 g., 0.123 mole) and the solution is stirred and heated at reflux two hours. The solution is poured into about 750 ml. ice water and the solid product is isolated by filtration, washed with petroleum ether and recrystallized twice from a benzene-acetone mixture with treatment with decolorizing charcoal. The off-white solid product is 4-(4-acetamidophenylthio)trifluoromethanesulfonanilide, m.p. 185.5°–187° C.

| Analysis: | %C | %H | %N |
|---|---|---|---|
| Calculated for $C_{15}H_{13}F_3N_2O_3S_2$: | 46.2 | 3.4 | 7.2 |
| Found: | 46.6 | 3.4 | 7.3 |

The following compounds are prepared using the method of Example 10.

3-acetamido-4-phenylthiotrifluoromethanesulfonanilide, m.p. 179°–182.5° C.

2-acetamido-4-phenylthiotrifluoromethanesulfonanilide, m.p. 185.5°–187° C.

EXAMPLE 11

4-Phenylthiotrifluoromethanesulfonanilide is dissolved in glacial acetic acid and treated with an equimolar amount of 70 percent nitric acid. The mixture is stirred one hour, then poured in water. The solid product is collected by filtration and recrystallized from ethanol to give 2-nitro-4-phenylthiotrifluoromethanesulfonanilide, m.p. 105.5°–107° C.

| Analysis: | %C | %H | %N |
|---|---|---|---|
| Calculated for $C_{13}H_9F_3N_2O_4S_2$: | 41.25 | 2.4 | 7.4 |
| Found: | 41.2 | 2.4 | 7.4 |

An additional compound prepared using the method of Example 11 is:

4-nitro-2-phenylthiotrifluoromethanesulfonanilide, m.p. 69°–70.5° C.

Examples 12-15 relate to the preparation of the compounds of Formula I by Method E.

EXAMPLE 12

Sodium 2-methyl-4-phenylsulfonyltrifluoromethanesulfonanilide in acetone is combined with an equimolar amount of ethyl chloroformate and the mixture is stirred at room temperature overnight. The mixture is filtered and the filtrate evaporated in vacuo to give N-ethoxycarbonyl-2-methyl-4-phenylsulfonyltrifluoromethanesulfonanilide, m.p. 118°–120° C.

The following compound is prepared using the method of Example 12.

N-ethoxycarbonyl-2-methyl-4-phenylthiotrifluoromethanesulfonanilide, m.p. 63°–64.5° C.

EXAMPLE 13

3-Phenylthiotrifluoromethanesulfonanilide (17.9 g., 0.0537 mole) is dissolved in acetone, treated with sodium carbonate (15.9 g., 0.15 mole) and stirred overnight. Methyl iodide is added and the mixture is stirred four hours. The mixture is filtered and the filtrate is evaporated in vacuo. The residue is extracted with dichloromethane, the extracts are washed with water, then the extracts are dried over magnesium sulfate. The mixture is filtered, then the solvent is evaporated in vacuo to give a residue which is distilled. The product is N-methyl-3-phenylthiotrifluoromethanesulfonanilide, b.p. 150° C./0.05 mm.

| Analysis: | %C | %H | %N |
|---|---|---|---|
| Calculated for $C_{14}H_{12}F_3NO_2S_2$: | 48.4 | 3.5 | 4.0 |
| Found: | 48.5 | 3.5 | 4.1 |

EXAMPLE 14

Sodium 2-methyl-4-phenylsulfonyltrifluoromethanesulfonanilide is dissolved in 1,2-dimethoxyethane by gentle heating. An equimolar amount of cyanogen bromide is dissolved in a small amount of 1,2-dimethoxyethane and added to the warm solution. The mixture is heated to its reflux temperature and maintained there for 1 hour. The mixture is filtered and the filtrate evaporated in vacuo to give the desired product, N-cyano-2-methyl-4-phenylsulfonyltrifluoromethanesulfonanilide, m.p. 89°–90.5° C.

EXAMPLE 15

Sodium 2-methyl-4-phenylsulfonyltrifluoromethanesulfonanilide in acetone is stirred while adding an equimolar amount of methanesulfonyl chloride, and stirring is continued overnight. The mixture is filtered, and the filtrate is evaporated in vacuo. The residue is dissolved in dichloromethane, and washed with dilute sodium hydroxide and with water. The product, N-methylsulfonyl-2-methyl-4-phenylsulfonyltrifluoromethanesulfonanilide, is recovered by evaporation of the dichloromethane followed by elution chromatography to give the product as an oil.

Examples 16 and 17 relate to the general methods for preparation of salts according to Formula I from the acid-form compounds.

EXAMPLE 16

Crude 3-phenylthioperfluoroethanesulfonanilide (prepared from perfluoroethanesulfonyl fluoride and 3-phenylthioaniline by Method A), diisopropyl ether and triethylamine are stirred for one hour at room temperature, the mixture is cooled with an ice bath, the solution is filtered and the salt is isolated by filtration, then recrystallized from isopropanol. The product is triethylammonium 3-phenylthioperfluoroethanesulfonanilide, m.p. 78.5°–81.5° C.

| Analysis: | %C | %H | %N |
|---|---|---|---|
| Calculted for $C_{14}H_{10}F_5NO_2S_2$: | 49.6 | 5.2 | 5.8 |
| Found: | 49.8 | 5.2 | 5.9 |

EXAMPLE 17

3-Phenylsulfonylperfluoroethanesulfonanilide is dissolved in acetone and treated with an equimolar amount of sodium carbonate. The solution is stirred overnight, then filtered and evaporated to dryness to give a white solid. The product, sodium 2-phenylsulfonylperfluoroethanesulfonanilide, is recrystallized from isopropanol and found to melt higher than 300° C.

| Analysis: | %C | %H |
|---|---|---|
| Calculated for $C_{14}H_9F_5NNaO_4S_2$: | 38.4 | 2.1 |
| Found: | 38.5 | 2.3 |

The following additional compounds of the invention are also prepared utilizing one of the preceding processes:

| Name | Melting Point (in ° C.) |
|---|---|
| 4-(3-methoxyphenylsulfinyl)trifluoromethanesulfonanilide | 130–133 |
| 4-(3-methoxyphenylsulfonyl)trifluoromethanesulfonanilide | 161–163 |
| 4-(4-t-butylphenylthio)-2-methyltrifluoromethanesulfonanilide | 101–104 |
| 4-(4-t-butylphenylsulfinyl)-2-methyltrifluoromethanesulfonanilide | 157–165 |
| 4-(4-t-butylphenylsulfonyl)-2-methyltrifluoromethanesulfonanilide | 189–193 |
| 3-(2,4-dimethylphenylthio)trifluoromethanesulfonanilide | 160–162° / 0.1 mm. |
| 3-(2,4-dimethylphenylsulfinyl)trifluoromethanesulfonanilide | 115–122 |
| 3-(2,4-dimethylphenylsulfonyl)trifluoromethanesulfonanilide | 106–111 |
| 3-(4-fluorophenylsulfinyl)trifluoromethanesulfonanilide | 92–94 |
| 3-(4-fluorophenylsulfonyl)trifluoromethanesulfonanilide | 108–112 |
| 3-(2-methylphenylsulfinyl)trifluoromethanesulfonanilide | 114–120 |
| 3-(3-methylphenylsulfinyl)trifluoromethanesulfonanilide | 98–101 |
| 3-(3-methylphenylsulfonyl)trifluoromethanesulfonanilide | 92–94 |
| 3-(4-methylphenylsulfinyl)trifluoromethanesulfonanilide | 103–104 |
| 4-(4-t-butylphenylsulfinyl)trifluoromethanesulfonanilide | 183–186 |
| 4-(3-methoxyphenylsulfinyl)2-methyltrifluoromethanesulfonanilide | 138–140 |
| 4-(3-methoxyphenylsulfonyl)-2-methyltrifluoromethanesulfonanilide | 135–137 |
| 4-(4-acetamidophenylthio)-2-methyltrifluoromethanesulfonanilide | 153–154 |
| 4-(2,4-dimethylphenylsulfinyl)-2-methyltrifluoromethanesulfonanilide | 157–160 |
| 3-(3-methoxyphenylthio)trifluoromethanesulfonanilide | 180–185° / 0.4 mm. |
| 3-(3-methoxyphenylsulfonyl)trifluoromethanesulfonanilide | 83–88 |
| 4-(2,5-dimethylphenylthio)trifluoromethanesulfonanilide | 163–165° / 0.5 mm. |
| 4-(2,5-dimethylphenylsulfinyl)trifluoromethanesulfonanilide | 164–168 |
| 4-(2,5-dimethylphenylsulfonyl)trifluoromethanesulfonanilide | 158–161 |

Examples 18–20 relate to the preparation of precursors of compounds of Formula I.

EXAMPLE 18

Freshly distilled thiophenol (24.8 g., 0.225 mole) and cuprous oxide (14.95 g., 0.10 mole as 96 percent active) are mixed under nitrogen atmosphere and refluxed in 95 percent ethanol (250 ml.) overnight. The bright yellow solid is filtered, separated from cuprous oxide and dried.

Cuprous thiophenolate (17.25 g., 0.10 mole) is dissolved with 3-bromonitrobenzene (20.2 g., 0.10 mole) in quinoline (100 ml.) and pyridine (20 ml.) and heated (under a nitrogen atmosphere) for 1 hour at 150° C. and 2 hours at 165°–170° C. The mixture is cooled, then poured into aqueous hydrochloric acid (160 ml. concentrated hydrochloric acid, 600 ml. water) and stirred two hours. The aqueous layer is decanted and extracted with diethyl ether (2 × 150 ml.). The ether layers are washed with 10 percent hydrochloric acid, water, concentrated ammonium hydroxide and water, then dried over magnesium sulfate. Fractional distillation yields 3-nitrophenyl phenyl sulfide (150°–180° C./0.7 mm.), which solidifies on scratching when suspended in petroleum ether.

EXAMPLE 19

A mixture of 2-methyl-5-nitroaniline (76.1 g., 0.50 mole) concentrated hydrochloric acid (75 ml.) and water (200 ml.) is heated briefly on a steam bath and an additional portion of hydrochloric acid (75 ml.) is added. This solution is cooled to and maintained at 0° to 5° C. and treated with sodium nitrite (35.5 g., 0.50 mole).

A solution of sodium hydroxide (50 g., 1.25 moles) in water (300 ml.) is heated to 90° C. under a nitrogen atmosphere and thiophenol (110 g., 1.0 mole) is added. This solution is treated with the solution of the diazonium compound in 20 ml. portions over a period of one hour. Finally the mixture is maintained at 90° C. for 1 hour, then acidified with hydrochloric acid. The solution is steam distilled, the residue is extracted with dichloromethane and the 2-methyl-5-nitrophenyl phenyl sulfide is separated by fractional distillation b.p. 148° C./0.15 mm. When recrystallized twice from hexane its m.p. is 65.5°–68° C.

EXAMPLE 20

A mixture of aluminum chloride (29.4 g., 0.22 mole) and benzene (250 ml.) is treated at reflux with 3-nitrobenzenesulfonly chloride (44.3 g., 0.250 mole) in benzene (50 ml.) over a period of 30 minutes. After eighty minutes additional aluminum chloride (9 g.,) is added. After an additional ninety minutes the mixture is cooled, then poured into a hydrochloric acid-ice mixture. This mixture is extracted with dichloromethane and the dichloromethane is then removed in vacuo. The solid 3-nitrophenyl phenyl sulfone is a pale yellow solid after recrystallization from ethanol, m.p. 77°–79° C.

EXAMPLE 21

Using the method of Example 1, 2-methylthio-4-phenylthioaniline is reacted with trifluoromethanesulfonic anhydride to provide 2-methylthio-4-phenylthiotrifluoromethanesulfonanilide.

EXAMPLE 22

Using the method of Example 1, 2-methylsulfinyl-4-phenylsulfonylaniline is reacted with trifluoromethanesulfonic anhydride to provide 2-methylsulfinyl-4-phenylsulfonyltrifluoromethanesulfonanilide.

EXAMPLE 23

The sodium salt of 3-amino-4-phenylthiotrifluoromethanesulfonanilide is reacted with ethyl chloroformate in acetone to provide 3-(ethoxycarbamoyl)-4-phenylthiotrifluoromethanesulfonanilide.

EXAMPLE 24

The sodium salt of 4-(4-aminophenylthio)trifluoromethanesulfonanilide is reacted with ethyl chloroformate in acetone to provide 4-(4-ethoxycarbamoylphenylthiotrifluoromethanesulfonanilide.

EXAMPLE 25

Using the method of Example 1, 4-(4-methylthiophenylthio)aniline is reacted with trifluoromethanesulfonic anhydride to provide 4-(4-methylthiophenylthiotrifluoromethanesulfonanilide.

EXAMPLE 26

Using the method of Example 1, 4-(4-methylsulfinylphenylsulfonyl)aniline is reacted with trifluoromethanesulfonic anhydride to provide 4-(4-methylsulfinylphenylsulfonyl)trifluoromethanesulfonanilide.

EXAMPLE 27

3-Amino-4-phenylthiotrifluoromethanesulfonanilide is reacted with formaldehyde and formic acid according to the well-known Eschweiler-Clarke reaction to provide 3-(N,N-dimethylamino)-4-phenylthiotrifluoromethanesulfonanilide.

EXAMPLE 28

4-(4-Aminophenylthio)trifluoromethanesulfonanilide is reacted with formaldehyde and formic acid according to the well-known Eschweiler-Clarke reaction to provide 4-(4-N,N-dimethylaminophenylthio)trifluoromethanesulfonanilide.

EXAMPLE 29

2-(4-Acetylphenylthio)aniline is reacted with trifluoromethanesulfonic anhydride according to the method of Example 1 to provide 2-(4-acetylphenylthio)trifluoromethanesulfonanilide.

EXAMPLE 30

The compound 2-bromo-4-phenylsulfonyltrifluoromethanesulfonanilide prepared according to the method of Example 5 from the compound of Example 7 is reacted with cuprous cyanide in N,N-dimethylformamide and the product obtained as pale yellow solid is 2-cyano-4-phenylsulfonyltrifluoromethanesulfonanilide, m.p. 162°–172° C.

| Analysis: | %C | %H | %N |
|---|---|---|---|
| Calculated for $C_{14}H_9F_3N_2O_4S_2$: | 43.1 | 2.3 | 7.2 |
| Found: | 42.7 | 2.3 | 7.1 |

EXAMPLE 31

4-[4-(N,N-dimethylsulfamoyl)phenylthio]aniline, prepared by reduction of 4-[4-(N,N-dimethylsulfamoyl)phenylthio]nitrobenzene is reacted with trifluoromethanesulfonic anhydride according to the method of Example 1 to provide 4-[4-(N,N-dimethylsulfamoyl)phenylthio]trifluoromethanesulfonanilide.

What is claimed is:

1. A compound of the formula

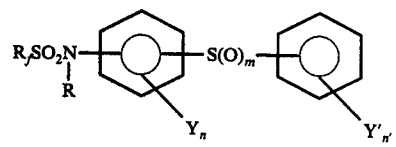

wherein $R_f$ is a lower perfluoroalkyl radical having one or two carbon atoms, R is cyano or

where R' is alkyl, m is 0–2, Y is halogen, alkyl, alkoxy, cyano, nitro, amino, alkanamido, hydroxy, dialkylamino, alkoxycarbamoyl, alkylthio, alkylsulfonyl, alkanoyl, dialkylsulfamoyl or alkylsulfinyl, Y' is fluorine, alkyl, alkoxy, cyano, nitro, amino, alkanamido, hydroxy, dialkylamino, alkoxycarbamoyl, alkylthio, alkylsulfonyl, alkanoyl, dialkylsulfamoyl or alkylsulfinyl and n and n' are independently 0–2, provided that the individual aliphatic groups appearing in the R, R', Y and Y' moieties contain from one to four carbon atoms each.

2. A compound according to claim 1 wherein $R_f$ is trifluoromethyl.

3. A compound according to claim 1 wherein Y is alkyl or halogen and Y' is alkyl or fluorine.

4. A compound according to claim 1 wherein $R_f$ is trifluoromethyl, R is

Y is halogen or alkyl of one or two carbon atoms in the 2 position with respect to the trifluoromethylsulfonamido group, the group

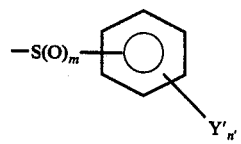

is oriented meta or para to the trifluoromethanesulfonamido group, m and n are 0–2, n' is 0–1 and Y' is fluorine.

5. A compound according to claim 4 wherein Y' is oriented para to the —S(O)$_m$— group.

6. A compound according to claim 4 wherein Y is oriented ortho to the perfluoroalkylsulfonamido group.

7. N-Carbethoxy-2-methyl-4-phenylsulfonyltrifluoromethanesulfonanilide according to claim 4.

8. N-Carbethoxy-2-methyl-4-phenylthiotrifluoromethanesulfonanilide according to claim 4.

9. A compound of the formula

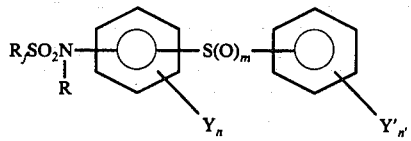

wherein $R_f$ is a lower perfluoroalkyl radical having one or two carbon atoms, R is hydrogen, alkyl, alkylsulfonyl, a horticulturally acceptable cation or

where R' is alkyl, m is 0-2, Y is halogen, alkyl, alkoxy, cyano, nitro, amino, alkanamido, hydroxy, dialkylamino, alkoxycarbamoyl, alkylthio, alkylsulfonyl, alkanoyl, dialkylsulfamoyl or alkylsulfinyl, Y' is fluorine, alkyl, alkoxy, cyano, nitro, amino, alkanamido, hydroxy, dialkylamino, alkoxycarbamoyl, alkylthio, alkylsulfonyl, alkanoyl, dialkylsulfamoyl or alkylsulfinyl and n and n' are independently 0-2, provided that the individual aliphatic groups appearing in the R, R', Y and Y' moieties contain from one to four carbon atoms each, and provided further that at least one Y or Y' group must be cyano or alkoxycarbamoyl.

10. A compound according to claim 9 wherein R is hydrogen, alkyl or a horticulturally acceptable cation.

11. A compound according to claim 9 wherein R is hydrogen.

12. A compound according to claim 9 wherein $R_f$ is trifluoromethyl.

13. A compound according to claim 9 wherein the $R_fSO_2NR-$ and

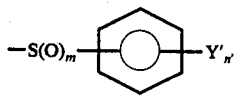

groups are oriented meta or para with respect to one another.

14. A compound according to claim 13 wherein R is hydrogen.

15. A compound according to claim 13 wherein R is a cation.

16. 2-Cyano-4-phenylsulfonyltrifluoromethanesulfonanilide according to claim 12.

* * * * *